US012751718B2

(12) United States Patent
Onushko et al.

(10) Patent No.: US 12,751,718 B2
(45) Date of Patent: Oct. 6, 2026

(54) LEFT ATRIAL APPENDAGE IMPLANT WITH DISTAL ENGAGEMENT ELEMENT

(71) Applicant: BOSTON SCIENTIFIC SCIMED, INC., Maple Grove, MN (US)

(72) Inventors: David John Onushko, Maple Grove, MN (US); Nicholas Lee Tassoni, Andover, MN (US); Christopher J. Clark, St. Michael, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 489 days.

(21) Appl. No.: 17/883,974

(22) Filed: Aug. 9, 2022

(65) Prior Publication Data

US 2023/0048873 A1 Feb. 16, 2023

Related U.S. Application Data

(60) Provisional application No. 63/233,113, filed on Aug. 13, 2021.

(51) Int. Cl.
*A61B 17/12* (2006.01)
*A61B 17/00* (2006.01)

(52) U.S. Cl.
CPC .. *A61B 17/12172* (2013.01); *A61B 17/12122* (2013.01); *A61B 2017/00597* (2013.01); *A61B 2017/00632* (2013.01)

(58) Field of Classification Search
CPC ........ A61B 17/12172; A61B 17/12122; A61B 2017/00597; A61B 2017/00632; A61B 2017/1205; A61B 17/12177
See application file for complete search history.

(56) References Cited

U.S. PATENT DOCUMENTS 4,619,246 A * 10/1986 Molgaard-Nielsen ........................ A61F 2/0108 128/899
5,375,612 A 12/1994 Cottenceau et al.
(Continued)

FOREIGN PATENT DOCUMENTS

CN 110025350 A 7/2019
EP 2074953 A1 7/2009
(Continued)

OTHER PUBLICATIONS

Invitation to Pay Additional Fees and, Where Applicable, Protest Fee for International Application No. PCT/US2013/070091 dated Feb. 3, 2014, 5 pages.
(Continued)

*Primary Examiner* — Andrew Restaino
(74) *Attorney, Agent, or Firm* — Seager, Tufte & Wickhem LLP

(57) ABSTRACT

A medical device for left atrial appendage closure includes a support frame with a proximal collar and a distal collar, where the support frame is actuatable from a first constrained configuration to a second radially expanded configuration. A membrane is disposed on at least a portion of the support frame, and an engagement element is coupled to the distal end region of the support frame. The engagement element extends distally from the support frame and is configured to engage an inner surface of the left atrial appendage and prevent the support frame from sliding along the inner surface of the left atrial appendage during implantation.

4 Claims, 10 Drawing Sheets

(56) References Cited

U.S. PATENT DOCUMENTS

| | | | | |
|---|---|---|---|---|
| 6,368,338 | B1 * | 4/2002 | Konya | A61B 17/12109 606/200 |
| 6,689,150 | B1 | 2/2004 | Van Tassel et al. | |
| 7,648,532 | B2 * | 1/2010 | Greenhalgh | A61F 2/2445 623/23.72 |
| 7,972,359 | B2 | 7/2011 | Kreidler | |
| 9,883,936 | B2 | 2/2018 | Sutton et al. | |
| 9,913,652 | B2 | 3/2018 | Bridgeman et al. | |
| 10,034,786 | B2 * | 7/2018 | Obradovic | A61F 2/848 |
| 2001/0000797 | A1 | 5/2001 | Mazzocchi | |
| 2002/0111647 | A1 | 8/2002 | Khairkhahan et al. | |
| 2005/0065589 | A1 * | 3/2005 | Schneider | A61B 17/12172 607/126 |
| 2005/0283186 | A1 | 12/2005 | Berrada et al. | |
| 2006/0052816 | A1 | 3/2006 | Bates et al. | |
| 2007/0066993 | A1 | 3/2007 | Kreidler | |
| 2007/0162048 | A1 | 7/2007 | Quinn et al. | |
| 2008/0033475 | A1 | 2/2008 | Meng | |
| 2009/0099647 | A1 | 4/2009 | Glimsdale et al. | |
| 2011/0054515 | A1 | 3/2011 | Bridgeman et al. | |
| 2011/0301630 | A1 | 12/2011 | Hendriksen et al. | |
| 2012/0239083 | A1 | 9/2012 | Kreidler | |
| 2015/0005810 | A1 * | 1/2015 | Center | A61B 17/12113 606/200 |
| 2016/0287261 | A1 | 10/2016 | Li et al. | |
| 2017/0224354 | A1 | 8/2017 | Tischler et al. | |
| 2017/0325824 | A1 | 11/2017 | Li et al. | |
| 2018/0338824 | A1 | 11/2018 | VanTassel et al. | |
| 2020/0305887 | A1 | 10/2020 | Lashinski et al. | |

FOREIGN PATENT DOCUMENTS

| | | | |
|---|---|---|---|
| EP | 3632337 | A1 | 4/2020 |
| JP | 2009160402 | A | 7/2009 |
| WO | 2005099365 | A2 | 10/2005 |
| WO | 2010148246 | A2 | 12/2010 |

OTHER PUBLICATIONS

International Search Report and Written Opinion dated Nov. 21, 2022 for International Application No. PCT/US2022/039804, 26 pages.

* cited by examiner

LEFT ATRIAL APPENDAGE IMPLANT WITH DISTAL ENGAGEMENT ELEMENT

CROSS-REFERENCE TO RELATED APPLICATIONS

This application claims the benefit of priority of U.S. Provisional Application No. 63/233,113 filed Aug. 13, 2021, the entire disclosure of which is hereby incorporated by reference.

TECHNICAL FIELD

The disclosure relates generally to medical devices and more particularly to medical devices for implantation into the left atrial appendage (LAA) of a heart.

BACKGROUND

Atrial fibrillation (AF) is the most common sustained cardiac arrhythmia, affecting over 5.5 million people worldwide. Atrial fibrillation is the irregular, chaotic beating of the upper chambers of the heart. Electrical impulses discharge so rapidly that the atrial muscle quivers, or fibrillates. Episodes of atrial fibrillation may last a few minutes or several days. The most serious consequence of atrial fibrillation is ischemic stroke. It has been estimated that up to 20% of all strokes are related to atrial fibrillation. Most atrial fibrillation patients, regardless of the severity of their symptoms or frequency of episodes, require treatment to reduce the risk of stroke. The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the amount of thrombi which may enter the blood stream from the left atrial appendage.

A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example medical device includes a medical device for left atrial appendage closure, comprising a support frame having a proximal end region with a proximal collar and a distal end region with a distal collar, wherein the support frame is actuatable from a first constrained configuration to a second radially expanded configuration, a membrane disposed on at least the proximal end region of the support frame, and an engagement element coupled to the distal end region of the support frame and extending distally beyond the distal end region of the support frame, the engagement element configured to engage an inner surface of the left atrial appendage and prevent the support frame from sliding along the inner surface of the left atrial appendage during implantation.

Alternatively or additionally to the embodiment above, the engagement element includes a plurality of atraumatic wires fixed to the distal collar.

Alternatively or additionally to any of the embodiments above, at least some of the plurality of atraumatic wires form wire loops extending distally of the distal end region.

Alternatively or additionally to any of the embodiments above, at least some of the plurality of atraumatic wires are fixed to a proximal face of the distal collar and extend proximally from the distal collar then curve around an outer edge of the distal collar to extend distally of the distal collar.

Alternatively or additionally to any of the embodiments above, at least some of the plurality of atraumatic wires are fixed to a distal face of the distal collar and extend distally from the distal collar.

Alternatively or additionally to any of the embodiments above, at least some of the plurality of atraumatic wires are fixed to the support frame.

Alternatively or additionally to any of the embodiments above, each of the plurality of atraumatic wires has a curved distal end.

Alternatively or additionally to any of the embodiments above, the plurality of atraumatic wires have different distal shapes.

Alternatively or additionally to any of the embodiments above, the support frame includes a plurality of wires having first ends fixed to the proximal collar and second ends passing through the distal collar and extending distal of the distal collar, wherein the second ends define the engagement element.

Alternatively or additionally to any of the embodiments above, the support frame includes a plurality of laser-cut struts, wherein the engagement element includes a plurality of atraumatic wires fixed to struts in the distal end region.

Alternatively or additionally to any of the embodiments above, the engagement element includes a plurality of atraumatic wires fixed to a distal third of the support frame.

Alternatively or additionally to any of the embodiments above, the engagement element includes a secondary distal collar fixed to the distal collar, the secondary distal collar including a plurality of atraumatic wires.

Alternatively or additionally to any of the embodiments above, the engagement element includes at least one atraumatic wire loop and at least one atraumatic wire.

Alternatively or additionally to any of the embodiments above, the engagement element includes a first plurality of atraumatic wires fixed to the distal collar and a second plurality of atraumatic wires fixed to the distal end region of the support frame.

Another example medical device for left atrial appendage closure comprises a support frame including a plurality of struts, the support frame having a proximal end region with a proximal collar, a medial region, and a distal end region with a distal collar, wherein the support frame is actuatable from a first constrained delivery configuration to a second deployed configuration in which at least the medial region is radially expanded to engage an inner wall of the left atrial appendage, a membrane disposed on at least the proximal end region of the support frame, and an engagement element including a plurality of atraumatic members extending distally beyond a distal endpoint of the support frame, the plurality of atraumatic members configured to engage the inner wall of the left atrial appendage and prevent the support frame from sliding along the inner wall during implantation.

Alternatively or additionally to the embodiments above, the proximal collar joins proximal ends of all of the plurality of struts and the distal collar joins distal ends of all of the plurality of struts.

Alternatively or additionally to any of the embodiments above, the plurality of atraumatic members are wires fixed to the distal end region of the support frame.

Alternatively or additionally to any of the embodiments above, the plurality of atraumatic members are wires passing through an interior of the support frame and extending through or around the distal end region or through the distal collar.

Alternatively or additionally to any of the embodiments above, at least some of the plurality of atraumatic members are fixed to a proximal face of the distal collar and extend proximally from the distal collar then curve around an outer edge of the distal collar to extend distally of the distal collar.

A further example medical device for left atrial appendage closure comprises a self-expanding support frame having a proximal end region with a proximal collar, a medial region, and a distal end region with a distal collar, wherein the support frame is actuatable from a first constrained delivery configuration to a second deployed configuration in which at least the medial region is radially expanded to engage an inner wall of the left atrial appendage, a membrane disposed on at least the proximal end region of the support frame, a plurality of anchors disposed on at least the medial region and extending radially outward therefrom, and an engagement element fixed to the distal end region of the support frame and extending distally therefrom, the engagement element configured to engage an inner surface of the left atrial appendage and prevent the support frame from sliding along the inner surface of the left atrial appendage during implantation.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
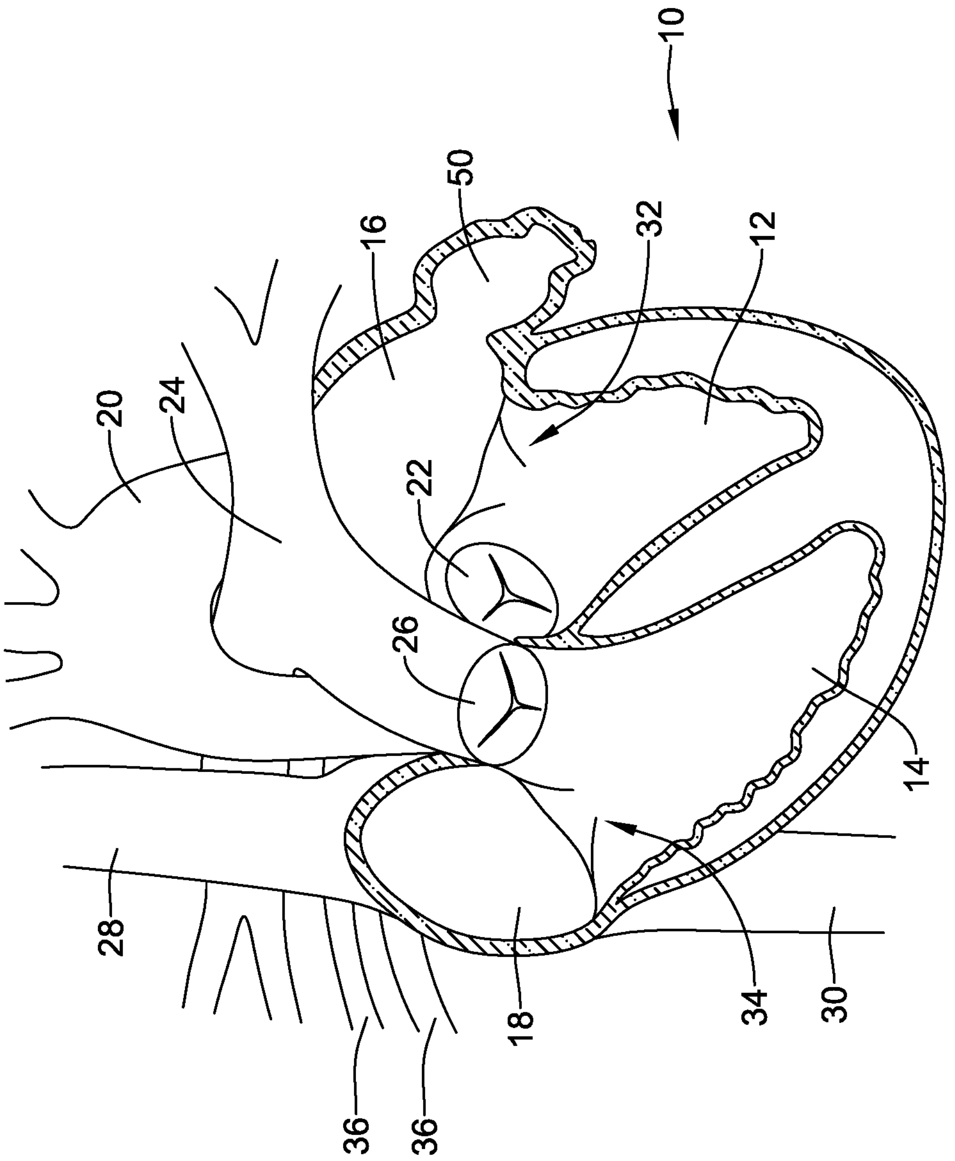
FIG. 1 is a schematic partial cross-sectional view of a heart.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently-such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

The occurrence of thrombi in the left atrial appendage (LAA) during atrial fibrillation may be due to stagnancy of the blood pool in the LAA. The blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. Further, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, a medical device has been developed that closes off the left atrial appendage from the heart and/or circulatory system, thereby lowering the risk of stroke due to thrombolytic material entering the blood stream from the left atrial appendage.

Turning to the drawings, FIG. 1 is a partial cross-sectional view of certain elements of a human heart 10 and some immediately adjacent blood vessels. A heart 10 may include a left ventricle 12, a right ventricle 14, a left atrium 16, and a right atrium 18. An aortic valve 22 is disposed between the left ventricle 12 and an aorta 20. A pulmonary or semi-lunar valve 26 is disposed between the right ventricle 14 and a pulmonary artery 24. A superior vena cava 28 and an inferior vena cava 30 return blood from the body to the right atrium 18. A mitral valve 32 is disposed between the left atrium 16 and the left ventricle 12. A tricuspid valve 34 is disposed between the right atrium 18 and the right ventricle 14. Pulmonary veins 36 return blood from the lungs to the left atrium 16. A left atrial appendage (LAA) 50 is attached to and in fluid communication with the left atrium 16.

Figure 2:
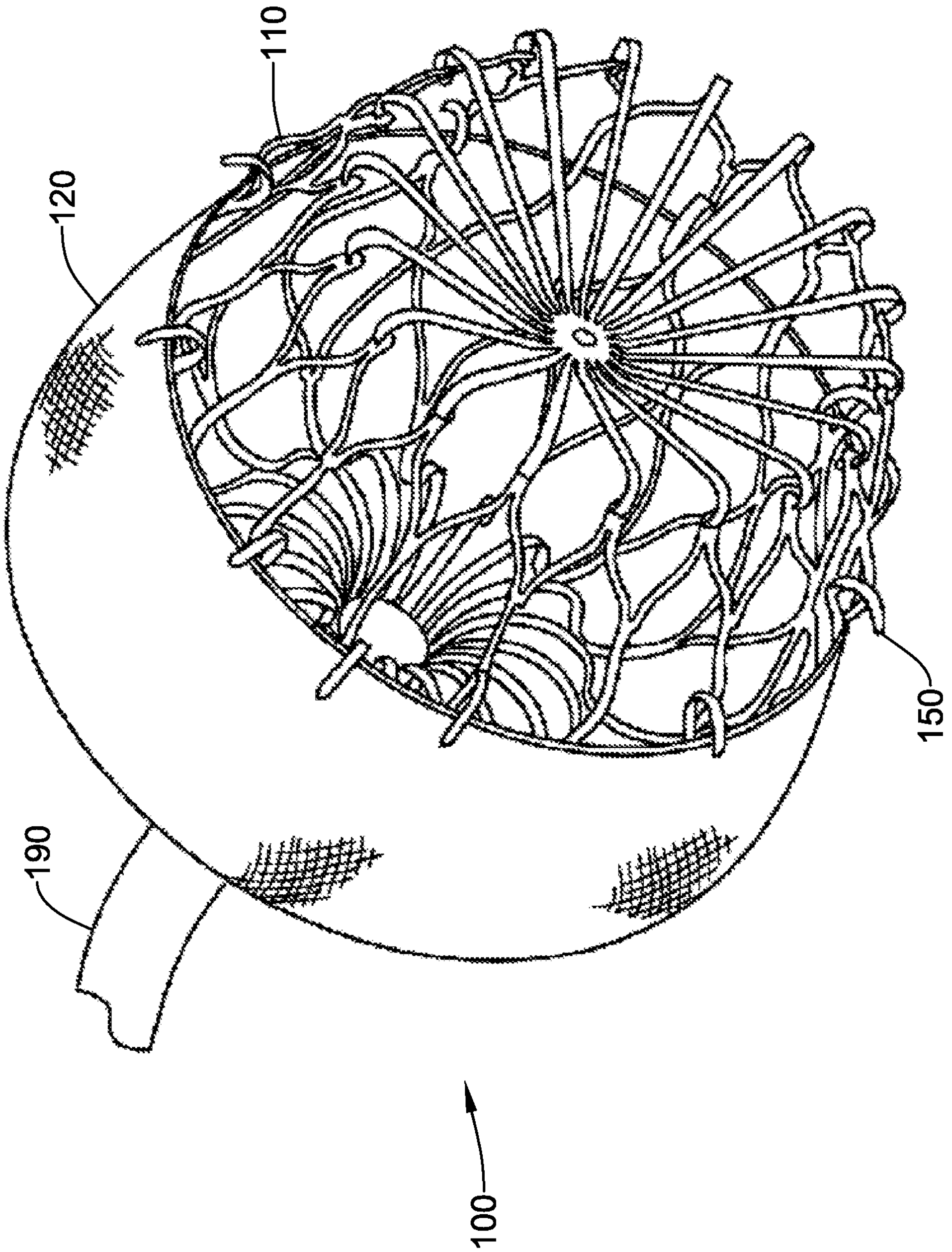
FIG. 2 Prior Art
FIGS. 2 and 3 illustrate example prior art implants.

FIG. 2 generally illustrates an example prior art implant 100, such as that disclosed in U.S. Pat. No. 9,913,652, which is herein incorporated by reference. The implant 100 may generally comprise a support frame 110 partially covered by a membrane 120. The support frame 110 may include a plurality of struts forming a lattice of generally diamond-shaped wire portions extending therefrom. The support frame 110 may include a plurality of barbs 150 extending radially outward from the support frame 110 to penetrate tissue and inhibit longitudinal movement of the deployed implant 100 in a proximal direction. The barbs 150 may be generally arranged in a single row about the circumference of the support frame 110. The barbs 150 may each be disposed immediately alongside one strut forming one side portion of one elongated generally diamond-shaped wire portion.

Figure 3:
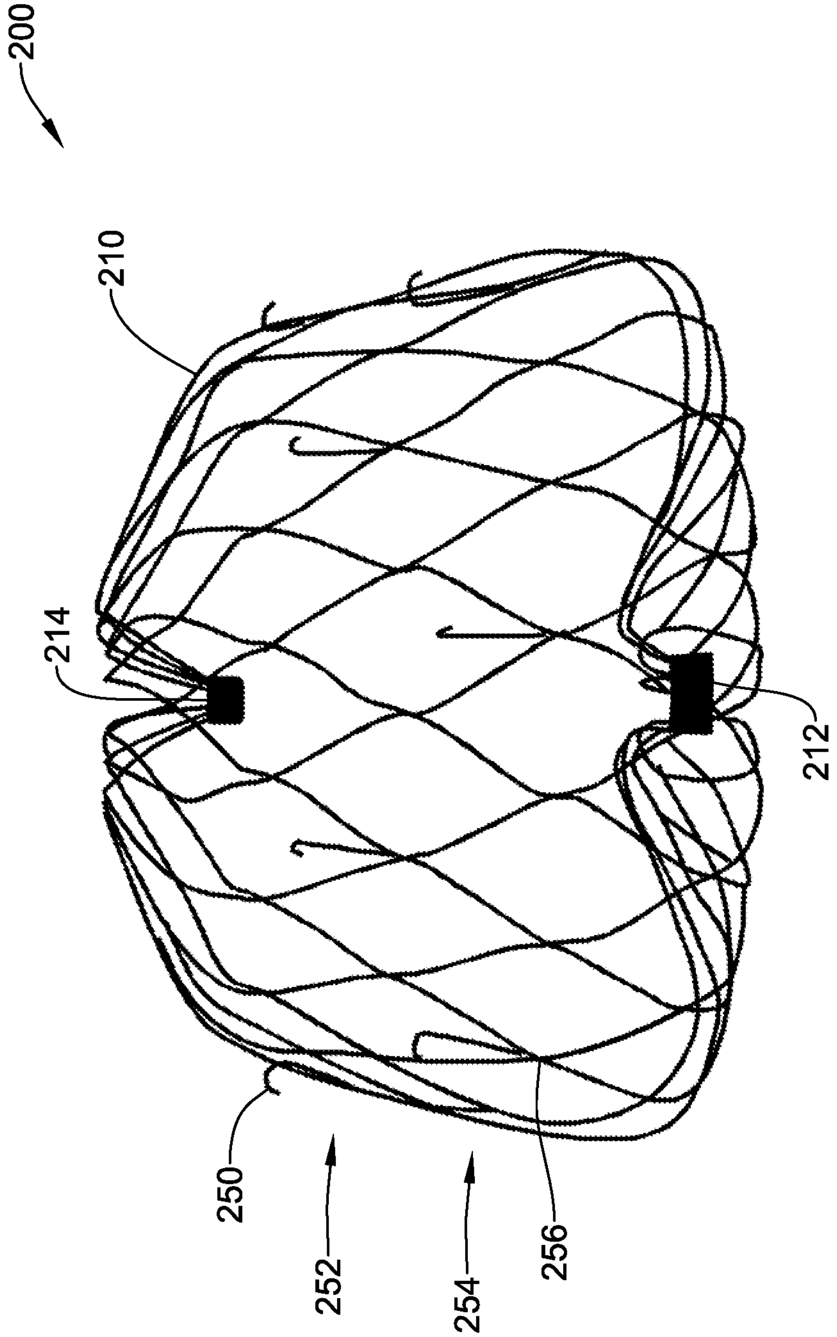
FIG. 3 Prior Art

FIG. 3 illustrates another prior art implant 200, such as that disclosed in U.S. Patent Application Publication No. US 2017/0224354 A1, which is herein incorporated by reference. The implant 200 may include a self-expanding monolithic support frame 210 extending from a proximal collar 212 to a distal collar 214. The distal collar 214 is also called a "puck." The support frame 210 may include a plurality of struts forming a lattice of generally diamond-shaped wire portions. In some embodiments, the proximal and distal ends of wire portions may be attached directly to the proximal and distal collars, respectively. The support frame 210 may include a plurality of anchors 250 provided to secure the implant 200 to the lateral wall of the left atrial appendage after deployment and thereby inhibit proximal movement of the implant 200 relative to the left atrial appendage. In some embodiments, the plurality of anchors 250 may be arranged into a first row 252 of anchors and a second row 254 of anchors disposed proximally of the first row 252 of anchors, wherein the first row 252 of anchors and the second row 254 of anchors cooperate to form a staggered pattern about the circumference of the support frame 210. Each of the plurality of anchors 250 may extend distally from a strut node junction 256, such that a hook portion of each of the plurality of anchors 250 is positioned within an interior of one generally diamond-shaped wire portion, spaced apart from the adjacent struts.

Figure 4:
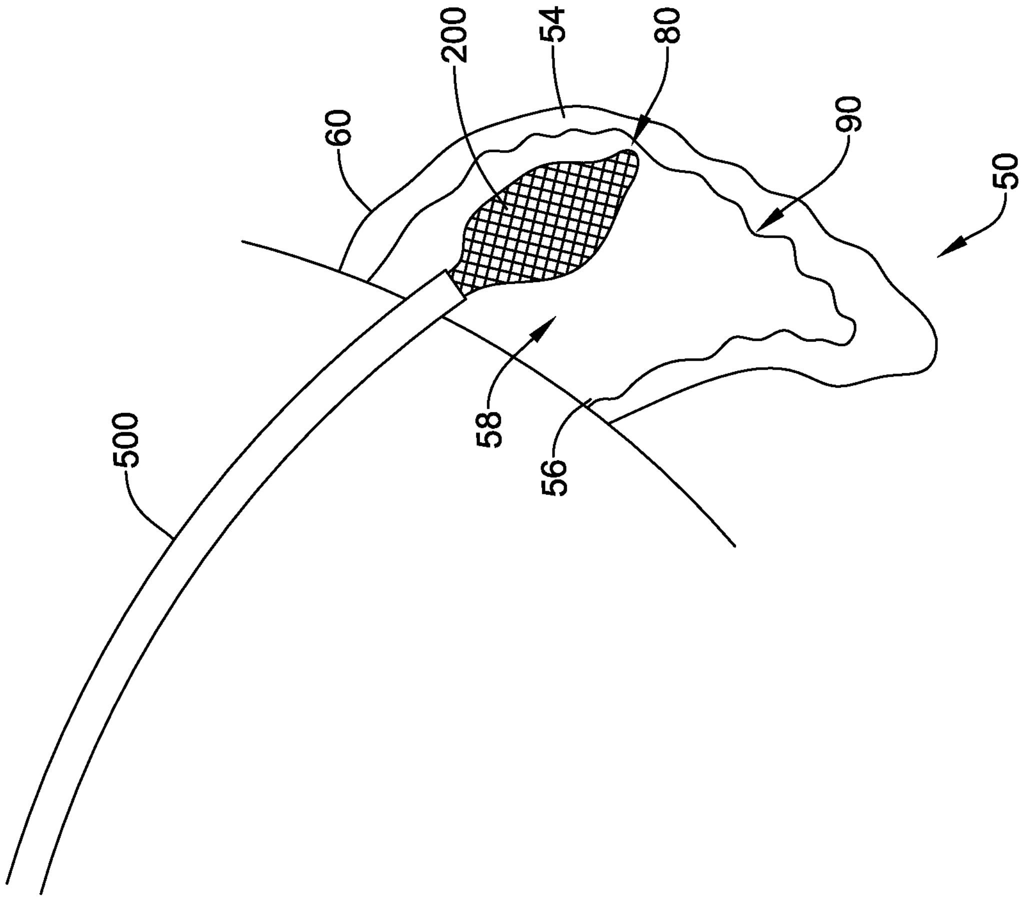
FIG. 4 is a partial cross-sectional view of the example prior art implant of FIGS. 2-3 in a partially deployed position.

The left atrial appendage 50 may have a complex geometry and/or irregular surface area. Those skilled in the art will recognize that the LAA illustrated in FIG. 4 is merely one of many possible shapes and sizes for the LAA, which may vary from patient to patient. Those of skill in the art will also recognize that the medical devices and methods disclosed herein may be adapted for various sizes and shapes of the LAA, as necessary. A left atrial appendage 50 may include a main body 60 with a lateral wall 54 and an ostium 56 forming a proximal mouth 58. In some embodiments, the left atrial appendage 50 may narrow quickly along the depth of the main body 60 or the left atrial appendage may maintain a generally constant lateral extent along a majority of depth of the main body 60. In some embodiments, the left atrial appendage 50 may include a distalmost region formed or arranged as a tail-like element associated with a distal portion of the main body 60.

Figure 5:
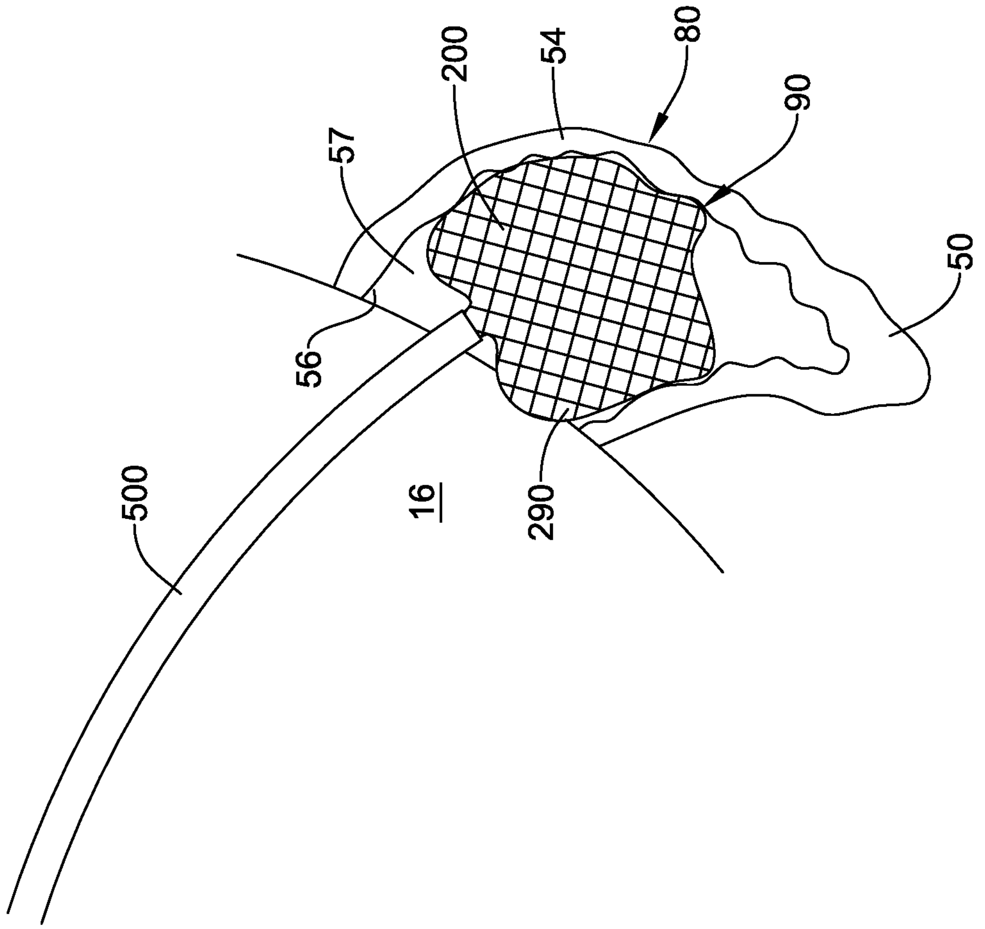
FIG. 5 illustrates the example prior art implant of FIG. 4 in a fully deployed position after slipping distally.

FIGS. 4 and 5 illustrate the "puck drop" or "posterior drop" that may occur during delivery of a prior art implant 200 on a catheter 500. The rounded ball-type structure of the prior art implant 200, as shown in FIG. 3, may improve safety of the implantation procedure by providing an atraumatic surface that can be advanced distally in a safe and controlled manner. However, this design does not provide a distal positioning and/or locating feature. This may result in "puck drop" or "posterior drop" of the implant, in which the puck or distal collar 214 drops during delivery, which may lead to poor implant position or poor anchoring. It may also contribute to proximal shift due to the watermelon seeding effect, where the rounded ball shaped distal end of the implant does not sit securely in between two pectinate muscles or small lobes of the left atrial appendage.

In order to place the implant 200 in a desired position to close off the ostium 56 of the LAA 50, the distal end of the implant 200 is positioned at a target position 80. Due to the rounded ball-type structure of the implant 200, the distal portion of the implant 200 may slide along the wall 54 of the LAA as the implant 200 is expanded, resulting in the distal end of the implant residing in a different position 90 when the implant 200 is fully expanded, as shown in FIG. 5. This "puck drop" or "posterior drop" may cause the implant 200 to be positioned incorrectly within the LAA. In some situations, the proximal end of the implant 200 may be offset relative to the ostium 56, causing a shoulder 290 on one side of the implant 200 to protrude into the left atrium 16, and/or uncovering a section 57 of the LAA which may cause a leak or incomplete seal.

Figure 6:
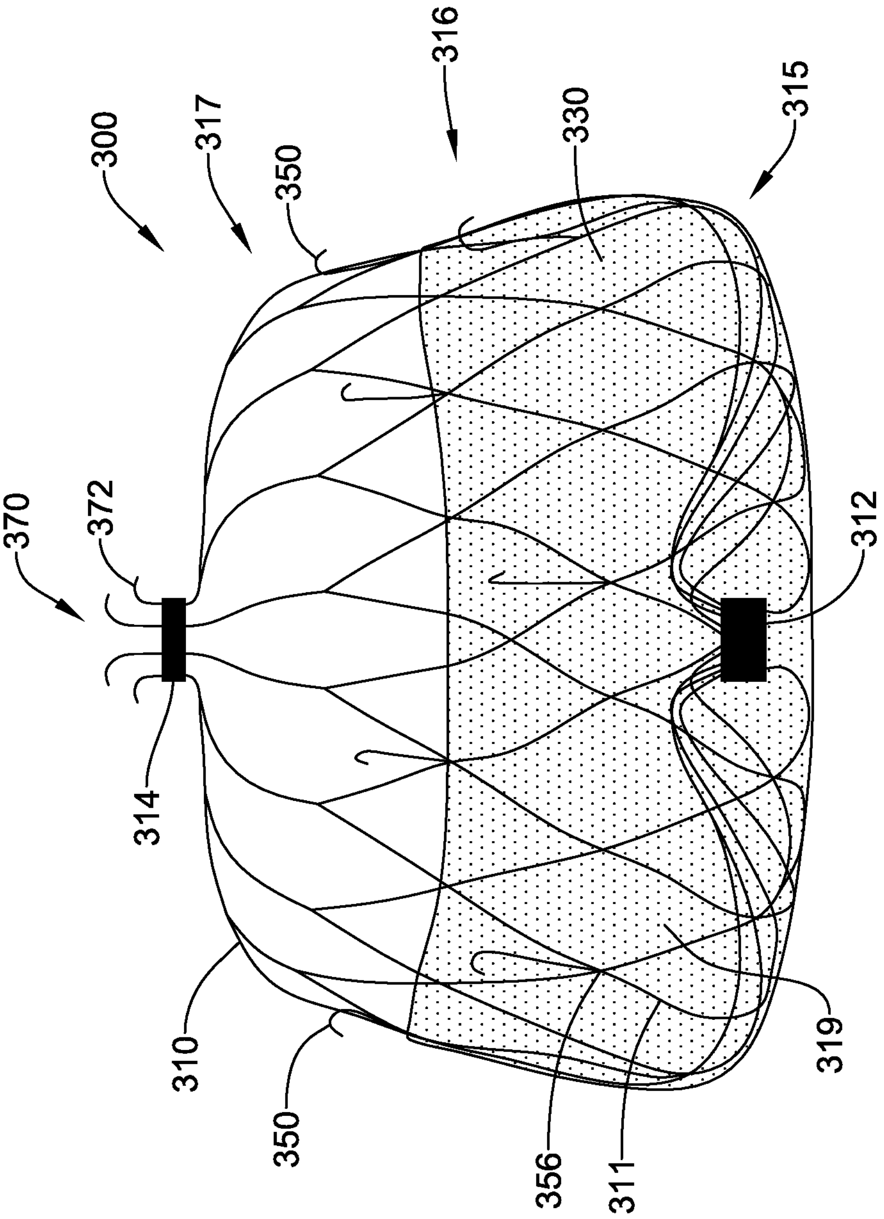
FIG. 6 is a perspective view of an example medical device according to the present disclosure.

The LAA implants would benefit from a structure providing improved resistance to lateral motion while maintaining the desired atraumatic distal end feature. The desired effect may be referred to as the implant having a "sticky distal" structure. FIG. 6 illustrates a cross-sectional view of an implant 300 with a "sticky distal" engagement element 370. The "sticky distal" engagement element 370 may provide a pivot point to fine tune the implant face orientation during deployment, utilizing the capabilities of the delivery system to fine tune and modify the implant position. For example, the "sticky distal" structure may be positioned to engage a specific lobe or pectinate of the LAA to prevent distal drop.

As shown in FIG. 6, the implant 300 may have a support frame 310 with a proximal end region 315 including a proximal collar 312, a medial region 316, and a distal end region 317 with a distal collar 314 or "puck." The support frame 310 may include a plurality of interconnected wires or struts 311 forming a lattice of generally diamond-shaped wire portions 319. The interconnected struts 311 may have first ends fixed directly to the proximal collar 312 and second ends fixed directly to the distal collar 314. The plurality of interconnected struts 311 may be wires or laser-cut struts. First ends of all of the struts 311 may be joined together by the proximal collar 312, and second ends of all of the struts 311 may be joined together by the distal collar 314. The implant 300 may be similar to implant shown in FIG. 3 but with the added engagement element 370 and with the distal end flipped so the struts 311 are fixed to the proximal face of the distal collar 314 instead of the distal face, as shown in FIG. 3. The flipped distal collar 314 configuration provides the advantage of having the engagement element 370 extend distally beyond a distalmost portion of the support frame 310.

The support frame 310 may be self-expandable and actuatable from a first constrained, elongated cylindrical delivery configuration to a second, fully radially expanded, deployed configuration as shown in FIG. 6. The support frame 310 in the second, fully radially expanded, deployed configuration may define a flattened ball shape with a circumferential side wall and proximal and distal faces extending transverse to a longitudinal axis extending through the proximal and distal collars 312, 314. The implant 300 may include a membrane 330 disposed on at least the proximal end region 315 of the support frame 310. In some embodiments, the membrane 330 may extend over at least a portion of the medial region 316. The membrane 330 may be disposed on the outer surface of the support frame 310. In other embodiments, the membrane 330 may be secured to the inner surface of the support frame 310.

The membrane 330 may be secured to the support frame 310 by any suitable attachment means, such as but not limited to, adhesive(s), sutures or thread(s), welding or soldering, or combinations thereof. In some embodiments, the membrane 330 may be permeable or impermeable to blood and/or other fluids, such as water. In some embodiments, the membrane 330 may include a polymeric membrane, a metallic or polymeric mesh, a porous filter-like material, or other suitable construction. In some embodiments, the membrane 330 may be permeable to blood while preventing thrombi (i.e. blood clots, etc.) from passing through the membrane 330 and out of the left atrial appendage into the blood stream. In some embodiments, the membrane 330 promotes endothelization after implantation, thereby effectively removing the left atrial appendage from the patient's circulatory system.

The support frame 310 may include a plurality of anchors 350 fixed to at least the medial region 316 of the support frame 310. The plurality of anchors 350 provided may secure the implant 300 to the lateral wall of the LAA after deployment and thereby inhibit proximal movement of the implant 300 relative to the LAA. In some embodiments, the anchors 350 may be arranged in a first row of anchors and a second row of anchors such that the plurality of anchors 350 forms a staggered pattern about the circumference of the support frame 310. Each of the plurality of anchors 350 may extend distally from a strut node junction 356, such that a hook portion of each of the plurality of anchors 350 is positioned within an interior of one generally diamond-shaped wire portions 319, spaced apart from the adjacent struts. The anchors 350 that are positioned in the region covered by the membrane 330 may extend through the membrane 330. The anchors 350 may be formed from the wires or cut from the struts 311 forming the support frame 310 such that the support frame 310 and anchors 350 are a single monolithic structure.

The engagement element 370 may be coupled to the distal end region of the support frame 310 and extend distally beyond the distal end of the frame. The engagement element 370 may be configured to engage the inner wall of the LAA and prevent the support frame 310 from sliding along the inner wall of the LAA during implantation. In the embodiment shown in FIG. 6, the engagement element 370 may include at least one atraumatic member 372 fixed to the distal collar and extending distally beyond a distal endpoint of the support frame 310. The atraumatic members 372 are illustrated in FIG. 6 as wires, however it will be understood that the atraumatic members 372 may form wire loops. Each of the atraumatic wires 372 may have a curved distal end such that the distal end tip points toward the proximal collar 312. In some embodiments, the engagement element 370 may include a plurality of atraumatic wires 372. The atraumatic wires 372 may be fixed to the distal collar 314. The atraumatic wires 372 may generally be weak and flexible to provide sufficient atraumatic engagement with the pectinate of the inner wall of the LAA to resist sliding of the implant 300 during deployment while not damaging the inner wall of the LAA. In some embodiments, second ends of some of the struts 311 pass through the distal collar 314 and extend distal of the distal collar 314 to define at least part of the engagement element 370.

Figure 7A:
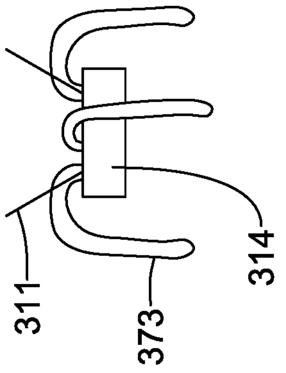
FIGS. 7A-7L illustrate example engagement elements according to the present disclosure.
Figure 7B:
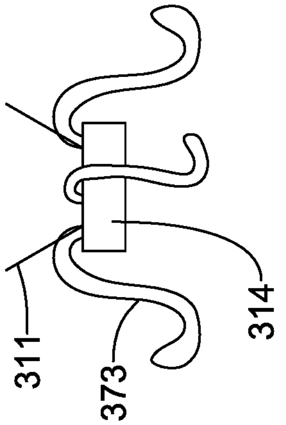
Figure 7C:
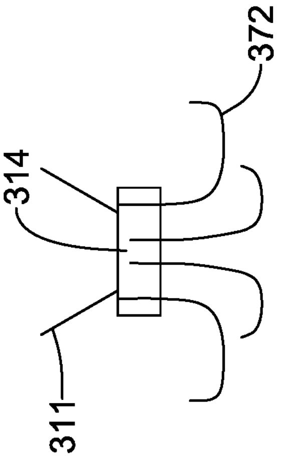
Figure 7D:
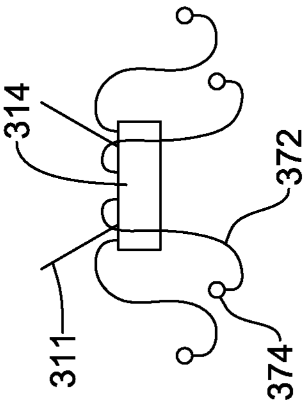
Figure 7E:
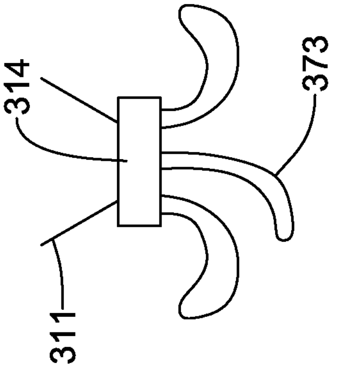
Figure 7F:
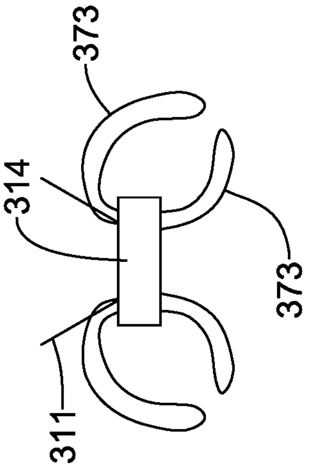
Figures 7G, 7H, 7I, 7J, 7K, 7L:
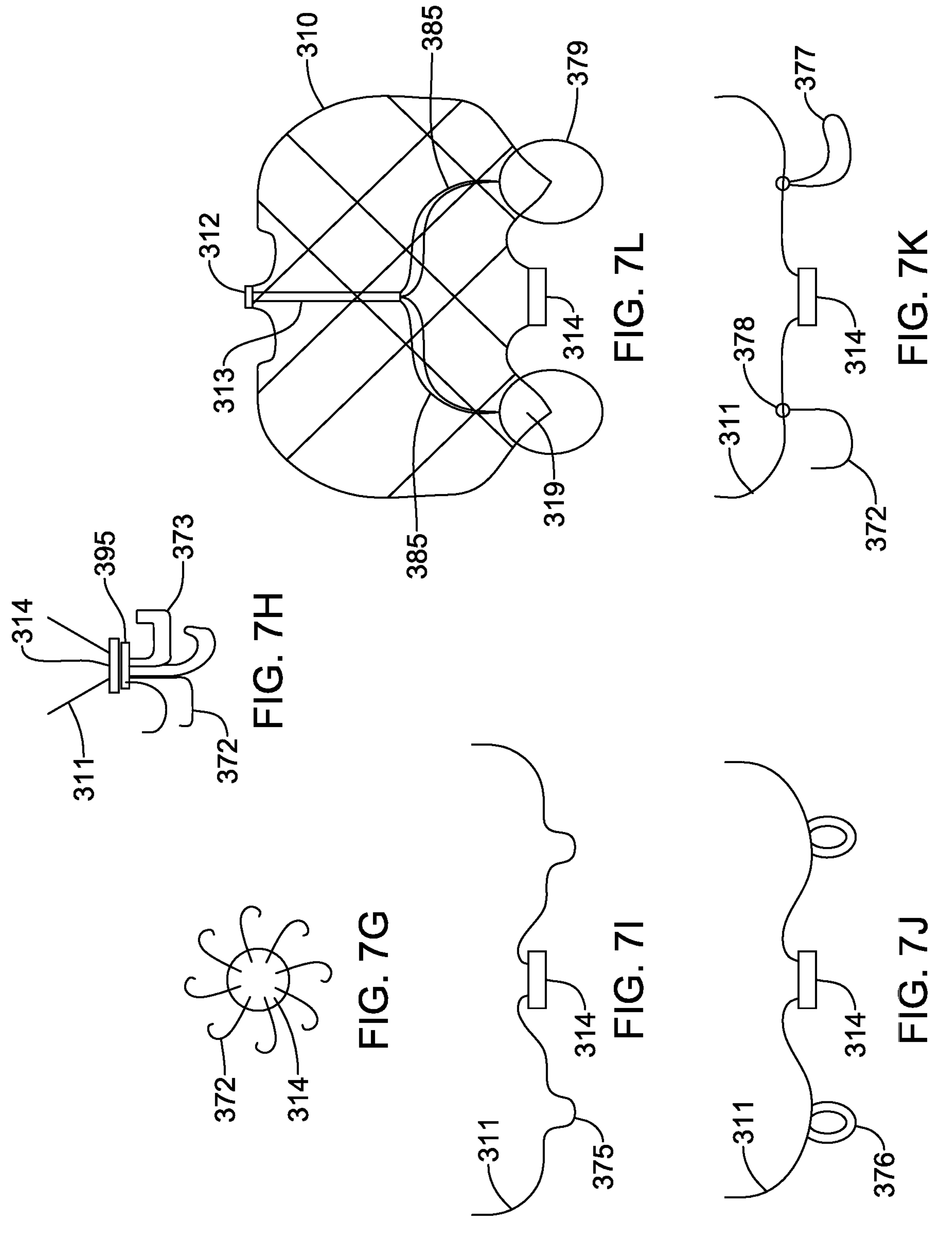

FIGS. 7A-7L illustrate a variety of engagement elements 370. In the figures, some of the engagement elements are illustrated as loops 373 (FIG. 7A) and others as atraumatic wires 372 (FIG. 7C). It will be understood that in every embodiment, the engagement elements may be either loops 373 or atraumatic wires 372 or a combination of loops and wires. FIGS. 7A-7F illustrate the engagement element 370 fixed to the distal collar 314. Only two of the plurality of struts 311 forming the support frame are shown for clarity. FIG. 7A illustrates a plurality of atraumatic wire loops 373 fixed to the proximal surface of the distal collar 314 and curving around the distal collar 314 and extending distally beyond the distal collar 314. In FIG. 7B, the atraumatic wire loops 373 include a distal curve with the end of the loop curved back toward the proximal collar. It will be understood that the plurality of atraumatic wires 372 and/or atraumatic wire loops 373 may have different distal shapes, and that a mixture of shapes may be present. FIG. 7C illustrates an embodiment in which a plurality of atraumatic wires 372 define the engagement element. The atraumatic wires 372 may be individual single atraumatic wires 372. The atraumatic wires 372 may be fixed to the distal face or proximal face of the distal collar 314 or they may extend through the distal collar 314. In some embodiments, the atraumatic wires 372 may be formed from the distal end regions of struts 311 forming the support frame. The atraumatic wires 372 may have distal ends curved back towards the proximal collar to provide an atraumatic engagement surface. In the embodiment illustrated in FIG. 7D, the engagement element 370 incudes a plurality of atraumatic wires 372 with ball structures 374 on their curved ends to provide additional atraumatic features. The atraumatic wires 372 may be fixed to the proximal surface of the distal collar 314 and extend proximally from the distal collar and then curve around the outer edge of the distal collar to extend distally of the distal collar, as illustrated. In other embodiments, the atraumatic wires 372 with ball structures 374 may be fixed to the distal surface of the distal collar 314 or they may extend through the distal collar as in FIG. 7C. The embodiment shown in FIG. 7E illustrates a plurality of atraumatic wire loops 373 fixed to the distal surface of the distal collar 314. In a further embodiment, the engagement element may include a first plurality of atraumatic wire loops 373 fixed to the proximal surface of the distal collar 314 and a second plurality of atraumatic wire loops 373 fixed to the distal surface of the distal collar 314, as shown in FIG. 7F. Alternatively, the loops 373 shown in FIG. 7F may be individual atraumatic wires. Any of the atraumatic wires 372 or atraumatic wire loops 373 described above may be disposed around the circumference of the distal collar 314, as illustrated in FIG. 7G. In another embodiment, the engagement element 370 may include a secondary distal collar 395 fixed to the distal face of the distal collar 314, as illustrated in FIG. 7H. Alternatively, the secondary distal collar 395 may be fixed to the proximal face of the distal collar 314. The secondary distal collar 395 may have a plurality of atraumatic wires 372 and/or atraumatic wire loops 373 in any configuration discussed above. The secondary distal collar 395 may be fixed to the distal collar 314 via welding, soldering, a press fit, adhesive, or any other secure fixation method.

In some embodiments, the engagement element 370 may include at least one single atraumatic wire 372 and at least one atraumatic wire loop 373. The atraumatic wires 372 and/or atraumatic wire loops 373 may be present in multiple shapes and positions to increase interaction with the LAA pectinate surface, reduce lateral motion, and add resistance to proximal motion as needed to reposition the implant. The engagement element is not configured to pierce or puncture or fix the implant to the wall of the LAA, but instead to help hold the position of the implant 300 during deployment and prevent the implant 300 from sliding along the wall of the LAA.

FIGS. 7I-7K illustrate embodiments in which the plurality of atraumatic wires are fixed to the support frame, and more particularly, to the struts 311 that define the support frame. In the embodiment illustrated in FIG. 7I, the struts 311 that define the support frame also form the engagement element. Protrusions or extensions 375 may be formed in the struts 311 of the distal end region of the support frame such that the extensions 375 and the struts 311 are monolithic structures. The protrusions or extensions 375 may be provided on at least the distal third of the support frame 310. In some examples, the protrusions or extensions 375 may be provided on only the distal end face of the implant, as illustrated in FIG. 7I. The Extensions 375 extend distally beyond the distal collar 314. In the embodiment illustrated in FIG. 7J, wire loops 376 are fixed to struts 311 defining the support frame, such as by welding, soldering, adhesive, or crimping. The wire loops 376 may extend around the struts 311 and be crimped in place. Relative motion of the wire loops 376 along the struts 311 may be inhibited by crimping the loops, adding one or more stop element on the struts 311, or by positioning the loops 376 between the diamond-shaped wire portions 319 defined by the support frame 310. See FIG. 7L. The wire loops 376 extend distally beyond the distal collar 314. In another embodiment, one or more atraumatic wires 372 and/or wire loops 377 may be fixed to the struts 311 forming the support frame, as illustrated in FIG. 7K. In some examples, the atraumatic wires 372 and/or wire loops may be welded to the struts 311 of the support frame or may be attached by sutures 378, as illustrated in FIG. 7K.

FIG. 7L illustrates an embodiment in which the engagement element 370 may be fixed to the proximal collar 312. The engagement element may include a proximal section 313 fixed to the proximal collar 312 and extending distally through the interior of the support frame 310, and a plurality of distal sections 385 extending from the proximal section 313, through or around the support frame 310, and forming loops 379. Directing the distal sections 385 through the support frame 310 and along the outside of the support frame 310 may provide additional resistance to lateral motion of the implant 300. In some embodiments, the loops 379 may extend through one of the of generally diamond-shaped wire portions 319 defined by the support frame 310. The loops 379 may extend distally of the distal collar 314. It will be understood that the engagement element 370 may include any combination of the structures illustrated in FIGS. 7A-7L.

Figure 8:
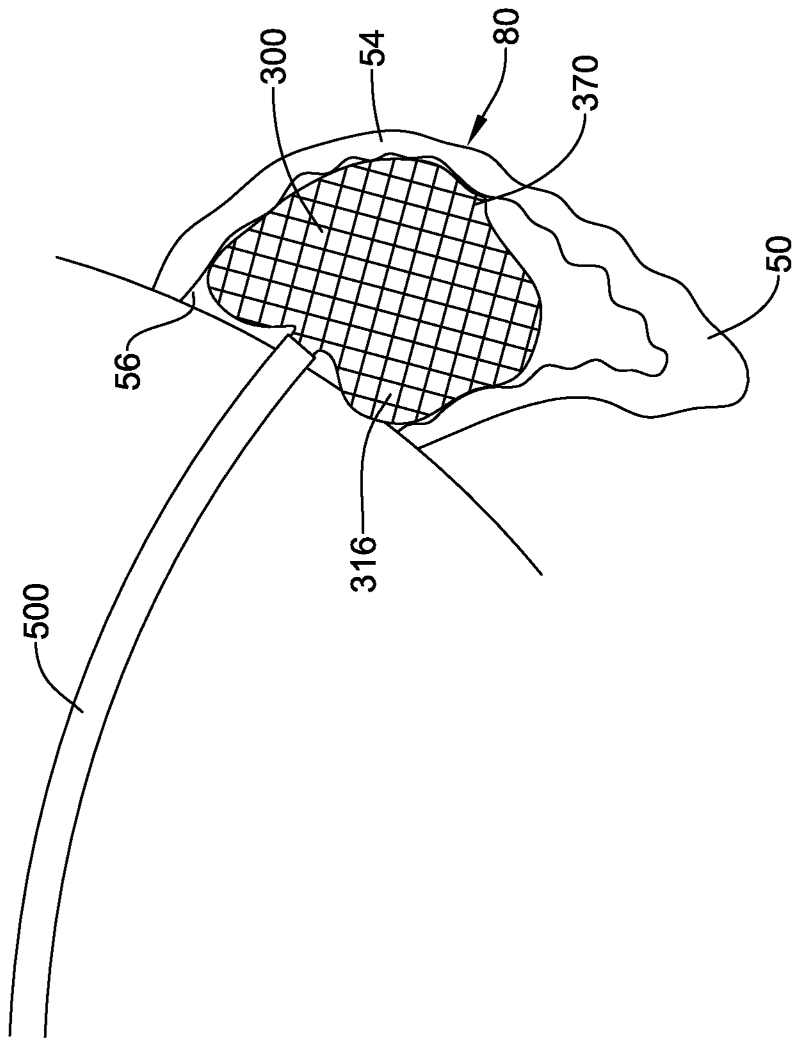
FIG. 8 illustrates the example medical device of FIG. 6 in a fully deployed position.

FIG. 8 illustrates the implant 300 delivered on a catheter 500 and fully expanded within the LAA 50, with the medial region 316 radially expanded and engaged with the wall of the LAA. The engagement element 370 on the distal end of the implant 300 is also engaged with the wall 54 of the LAA to keep the implant in the desired target position 80 during deployment. The engagement element 370 prevents the implant 300 from sliding during deployment, and allows the implant 300 to be seated within the ostium 56 as desired.

In some embodiments, the engagement element 370, particularly the atraumatic wires 372 or atraumatic wire loops 373 may be metal, polymer, or a combination or mixture thereof. In one embodiment, the atraumatic wires 372 or atraumatic wire loops 373 may be 0.005 inch round polyethylene terephthalate (PET) with a bend rigidity of about 0.00001 $\text{lbf/in}^2$. In another embodiment, the atraumatic wires 372 or atraumatic wire loops 373 may be made of 0.020 inch×0.008 inch rectangular nitinol with a bend rigidity of about 0.010 $\text{lbf/in}^2$.

$$\text{Bend Rigidity} = E * I \ (E = \text{elastic modulus}, I = \text{moment area of inertia})$$

The atraumatic wires 372 or atraumatic wire loops 373 may have a wide range of bend rigidity depending on the material and the geometry of the part. The engagement element 370 has sufficient rigidity to prevent it from completely collapsing and allowing the implant 300 to slide along the wall of the LAA, but is flexible and deformable enough to provide atraumatic engagement with the wall of the LAA and prevent the engagement element 370 from extending completely through the wall of the LAA.

Figure 9:
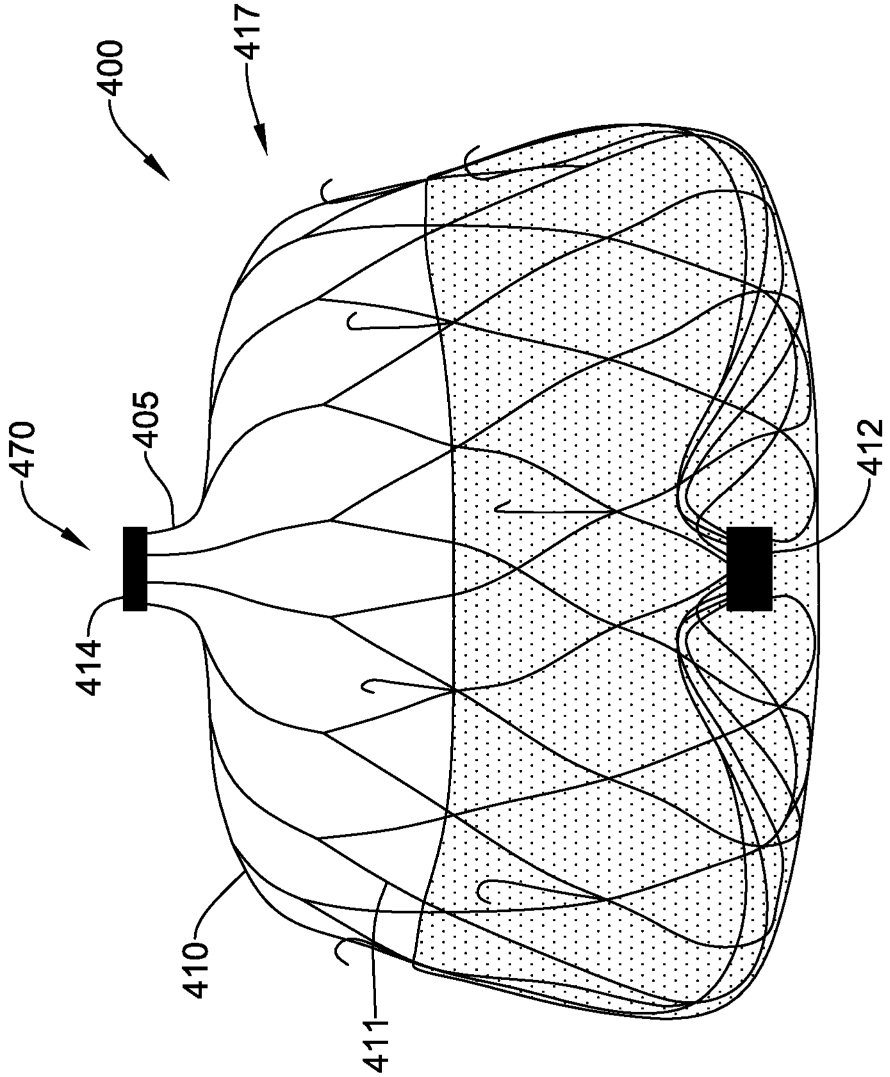
FIG. 9 illustrates another example medical device according to the present disclosure.

FIG. 9 illustrates another example implant 400. The implant 400 may include a support frame 410 and proximal collar 412 similar to the support frame 310 and proximal collar 312 of implant 300 shown in FIG. 6. The implant 400 may include an engagement element 470 defined by a distal collar 414 spaced apart distally from the distal end region 417 of the support frame 410 by a neck 405. The neck 405 may be defined by a plurality of elongated struts 411 forming the support frame 410. The engagement element 470 may be devoid of any atraumatic wires or loops, as shown in FIG. 9. In other embodiments, the engagement element 470 may include one or more atraumatic wires 372 and/or wire loops 373 as discussed above.

In some embodiments, a method of manufacturing the implant 300 may include the steps of:

- obtaining an elongate tubular member having a lumen extending therethrough and an annular ring member;
- laser cutting the tubular member to form a proximal collar, a plurality of struts, a plurality of anchors interspersed among the plurality of struts, and a plurality of free distal ends, as a single monolithic structure;
- forming the plurality of struts into a lattice of generally diamond-shaped wire portions;
- fixedly attaching the plurality of free distal ends to the annular ring member to form a distal collar;
- fixedly attaching a plurality of atraumatic wires and/or wire loops to the distal collar to form an engagement element; and
- attaching a membrane over at least a portion of the plurality of struts such that the plurality of anchors extends through the membrane.

In some embodiments, the LAA implant 300 (and variations, systems or components thereof disclosed herein) may be made from a metal, metal alloy, ceramics, zirconia, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "superelastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the LAA implant 300 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the LAA implant 300 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the LAA implant 300 (and variations, systems or components thereof disclosed herein) to achieve the same result.

In some embodiments, the LAA implant 300 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the LAA implant 300 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)).

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

We claim:

1. A medical device for a left atrial appendage closure, comprising:

only one proximal collar and only one distal collar;

a support frame including a plurality of struts, the support frame having a proximal end region with the proximal collar, a medial region, and a distal end region with the distal collar, wherein distal ends of all of the plurality of struts are coupled directly to the distal collar, wherein the support frame is actuatable from a first constrained delivery configuration to a second deployed configuration in which at least the medial region is radially expanded to engage an inner wall of the left atrial appendage, wherein the support frame in the second deployed configuration defines a flattened ball shape with a circumferential side wall and proximal and distal faces extending transverse to a longitudinal axis extending through the proximal and distal collars;

a membrane disposed on at least the proximal end region of the support frame; and an engagement element including a plurality of atraumatic members extending distally beyond a distal endpoint of the support frame, the plurality of atraumatic members configured to engage the inner wall of the left atrial appendage and prevent the support frame from sliding along the inner wall during implantation, wherein at least some of the plurality of atraumatic members are first wires fixed directly to the plurality of struts on the distal face of the support frame, spaced radially inward from the circumferential side wall.

2. The medical device of claim 1, wherein at least some of the plurality of atraumatic members are second wires fixed directly to the distal collar and extending distally therefrom.

3. The medical device of claim 1, wherein at least some of the plurality of atraumatic members are additional wires fixed to the proximal collar and passing through an interior of the support frame and extending through or around the distal end region or through the distal collar.

4. The medical device of claim 1, wherein at least some of the plurality of atraumatic members are fixed to a proximal face of the distal collar and extend proximally from the distal collar then curve around an outer edge of the distal collar to extend distally of the distal collar.

* * * * *